United States Patent
Milles

(10) Patent No.: US 7,481,217 B2
(45) Date of Patent: Jan. 27, 2009

(54) METHOD AND APPARATUS FOR EVACUATING NITROUS OXIDE

(75) Inventor: Maano Milles, Berkeley Heights, NJ (US)

(73) Assignee: University of Medicine and Dentistry of NJ, New Brunswick, NJ (US)

(*) Notice: Subject to any disclaimer, the term of this patent is extended or adjusted under 35 U.S.C. 154(b) by 443 days.

(21) Appl. No.: 10/519,959

(22) PCT Filed: Jul. 25, 2003

(86) PCT No.: PCT/US03/23556

§ 371 (c)(1),
(2), (4) Date: Dec. 30, 2004

(87) PCT Pub. No.: WO2004/010892

PCT Pub. Date: Feb. 5, 2004

(65) Prior Publication Data

US 2006/0032509 A1 Feb. 16, 2006

(51) Int. Cl.
A61M 15/00 (2006.01)
A61M 16/10 (2006.01)
A62B 7/10 (2006.01)
A62B 19/00 (2006.01)
A62B 23/02 (2006.01)

(52) U.S. Cl. .............. 128/205.12; 128/203.12; 128/910

(58) Field of Classification Search ............ 128/205.12, 128/205.19, 203.12, 910
See application file for complete search history.

(56) References Cited

U.S. PATENT DOCUMENTS

| | | | |
|---|---|---|---|
| 3,804,086 A * | 4/1974 | Agnew ................. 128/202.19 |
| 3,955,570 A | 5/1976 | Hutter, III ............... 128/142.7 |
| 4,151,843 A | 5/1979 | Brekke et al. .............. 128/203 |
| 4,265,239 A * | 5/1981 | Fischer et al. ......... 128/205.17 |
| 4,651,727 A * | 3/1987 | Howorth ............... 128/201.23 |
| 4,895,172 A * | 1/1990 | Lindkvist .................... 128/863 |
| 4,920,768 A * | 5/1990 | Cares et al. ................ 68/18 R |
| 5,018,519 A | 5/1991 | Brown .................. 128/203.29 |
| 5,033,464 A | 7/1991 | Dlcastilho ............. 128/205.19 |
| 5,046,491 A * | 9/1991 | Derrick ................ 128/200.24 |
| 5,195,512 A * | 3/1993 | Rosso ................... 128/200.24 |
| 5,419,317 A * | 5/1995 | Blasdell et al. ........ 128/205.19 |
| 5,513,632 A | 5/1996 | Nepon et al. .......... 128/205.19 |

(Continued)

OTHER PUBLICATIONS

Adams, "A Scavenging System and Expiratory Valve for Use in Out-Patient Dental Anaesthesia," British Dental Journal, Jul. 20, 1976, pp. 55-56.

(Continued)

Primary Examiner—Justin R Yu
Assistant Examiner—Kristen C Matter
(74) Attorney, Agent, or Firm—Klauber & Jackson

(57) ABSTRACT

An anesthetic gas scavenging system is provided. The system includes a housing having one or more apertures placed proximate to a patient's mouth and a vacuum source interconnected with the housing for excavating anesthesia exhaled by the patient. The housing can take the form of a circular tube and can be positioned to rest about a patient's neck. The housing can have closed ends attachable together about a patient's neck. Alternatively, the housing can take on other desired shapes, and can be suspended on a strap about a patient's neck to rest on the patient's chest.

9 Claims, 7 Drawing Sheets

U.S. PATENT DOCUMENTS

| | | | |
|---|---|---|---|
| 5,715,813 A | 2/1998 | Guevrekian | 128/205.12 |
| 6,076,524 A * | 6/2000 | Corn | 128/205.12 |
| 6,202,645 B1 | 3/2001 | Brown | 128/205.24 |
| 6,305,375 B1 | 10/2001 | Brown | 128/205.24 |

OTHER PUBLICATIONS

Brodsky, et al., "Exposure to Nitrous Oxide and Neurologic Disease Among Dental Professionals," Anesthesia and Analgesia, vol. 60, No. 5, May 5, 1981, pp. 297-301.

Cohen, et al., "Occupational Disease in Dentistry and Chronic Exposure to Trace Anesthetic Gases," JADA, vol. 101, 1980, pp. 21-31.

Hallonsten, "Nitrouos Oxide Scavenging in Dental Surgery," Swed Dent J, vol. 6, pp. 203-213, 1982.

Hallonsten, "Nitrouos Oxide Scavenging in Dental Surgery," Swed Dent J, vol. 6, pp. 215-223, 1982.

Kugel, et al., "Nitrous Oxide and Occupational Exposure: It's Time to Stop Laughing," Anesth Prog, vol. 36, pp. 252-257, 1989.

Parbrook, "Toxicity of Nitrous Oxide," The Metabolic Effects of Anaesthesia, pp. 79-80.

Rowland, et al., "Reduced Fertility Among Women Employed as Dental Assistants Exposed to High Levels of Nitrous Oxide," The New England Journal of Medicine, vol. 327, No. 14, pp. 993-997.

Swenson, "Scavenging of Dental Anesthetic Gases," J Oral Surgery, vol. 34, Mar. 1976, pp. 207-214.

Nitrous Oxide/Oxygen Scavenger System, printout from website: http://www.porterinst.com/conscav.html (2 pages).

* cited by examiner

METHOD AND APPARATUS FOR EVACUATING NITROUS OXIDE

BACKGROUND OF THE INVENTION

1. Field of the Invention

The present invention relates to a method and apparatus for evacuating nitrous oxide exhaled by a patient, and more specifically, to an apparatus that can be positioned on a patient to evacuate exhaled nitrous oxide.

2. Related Art

Nitrous oxide is an anesthetic gas widely used in dental offices. It is typically administered with oxygen and functions primarily as a sedative to reduce anxiety during dental procedures. The exposure limit for nitrous oxide recommended by the National Institute for Occupational Safety and Health (NIOSH) is 25 ppm for an average exposure time of 8 hours. Levels of nitrous oxide found in dental offices may be substantially higher, typically ranging from about 100 ppm in offices that use anesthetic gas scavenging equipment to over 1000 ppm in offices that do not use such equipment.

Increased general heath problems and reproductive difficulties associated with exposure of non-patients to occupational levels of nitrous oxide have been described in scientific, medical and dental literature. Exposure to high levels of nitrous oxide typically found in dental offices has been found to adversely affect fertility in women (Roland A S et al., *N Engl J Med,* 1992, 327:993-997). Long-term exposure of male dentists to nitrous oxide in the dental operatory has been correlated with an increased incidence in liver and renal disease, spontaneous abortion in their wives, and general and non-specific neurologic disease. Among female chairside assistants, the association between long-term occupational exposure to nitrous oxide and these same general health and reproductive problems is more pronounced (Cohen E N et al., *JADA,* 1980, 101:21-31). It was found that dental professionals and assistants who worked with nitrous oxide exhibited a three- to four-fold increase in the incidence of neurological complaints, for example, numbness, tingling and/or muscle weakness, compared to non-anesthetic exposed dental employees (Brodsky J B et al., *Anesthesia and Analgesia,* 1981, 60:297-301).

A particular problem in the dental office environment is that the patient's mouth is open and nitrous oxide is released through the patient's mouth during respiration and conversation. This leads to the undesirable exposure of dental office personnel to excess levels of nitrous oxide.

In the past, it has been known to evacuate exhaled or trace concentrations of nitrous oxide by a combination delivery and evacuation system. One such system, sold by Porter Instrument Company, Inc., Hatfield, Pa., and known as the Porter/brown Scavenger (breathing circuit) System, provides a first outer mask for the delivery of nitrous oxide and a second inner mask nested within the outer mask for evacuation of exhaled nitrous oxide. The masks are designed to fit around the nose of a patient. However, these mask-based evacuation systems are limited to the evacuation of anesthetic gases that are exhaled by the nose, and do not evacuate gases that are exhaled from the mouth, or gases that otherwise leak from the system.

Accordingly, what is needed, but has not heretofore been provided, is an effective method and apparatus for evacuating nitrous oxide exhaled or released from a patient's mouth, or otherwise leaks from the nitrous oxide delivery or evacuation system, in a dental operatory which does not interfere with the performance of the dental procedure.

SUMMARY OF THE INVENTION

The present invention relates to an anesthesia scavenging apparatus. The apparatus includes a housing having one or more vents and an outlet. A vacuum source is connected to the outlet. The housing is positioned proximate to a patient. The housing can be in the form of a tube or other configuration, and can be made of a lightweight, flexible material with apertures. In one embodiment, the housing comprises perforated plastic tubing. The length of the tubing can be varied. The tube can be draped over a patient's shoulder and chest. The tube may be circular in shape for placement about the patient's neck. The tube can be continuous and placed over a patient's head and about the patent's neck. Alternatively, the ends of the tube can be closed and the ends can be attached by fasteners. In another embodiment, the housing comprises a short tube with closed ends that rests on a patient's chest. In this embodiment, the housing is suspended about the patient's neck by a band interconnectable with the housing.

The present invention also relates to a method of removing anesthetic gas exhaled by a patient being administered anesthetic gas, or gas which otherwise leaks from the anesthetic gas delivery or evacuation system, comprising the steps of placing a perforated housing proximate to a patient, connecting the perforated housing to a vacuum, and applying a vacuum to remove exhaled or leaked anesthetic gas.

BRIEF DESCRIPTION OF THE DRAWINGS

Other important objects and features of the invention will be apparent from the following Detailed Description of the Invention taken in connection with the accompanying drawings in which.

DETAILED DESCRIPTION OF THE INVENTION

For the purpose of illustration, embodiments of the present invention are shown in FIGS. 1-6, wherein like numbers are used to designate like parts throughout the drawings. In general, the present invention relates to a nitrous oxide scavenging apparatus comprising a housing with one or more vents. The housing also has an outlet connected to a vacuum. The housing is placed proximate to a patient, for example, near the mouth of the patient to remove exhaled nitrous oxide gas. The phrase "proximate to the mouth of a patient," as used herein means the area below the mouth and about the neck and chest of a patient, i.e., the area where nitrous oxide flows after it is exhaled. The apparatus removes nitrous oxide exhaled by a patient through the mouth due to talking or breathing, or gas otherwise released during administration of the anesthetic. While the method and apparatus of the present invention are discussed primarily with reference to nitrous oxide, it should be understood that this invention can be used with any other inhalation anesthetic agents used, or mixes thereof.

Figure 1:
FIG. 1 shows a nitrous oxide scavenger apparatus according to the present invention positioned on a patient.

FIG. 1 shows the nitrous oxide evacuating apparatus 10 positioned about a patient seated in a dental chair. Vacuum line 60 is used to connect the evacuating apparatus 10 to a vacuum.

Figure 2:
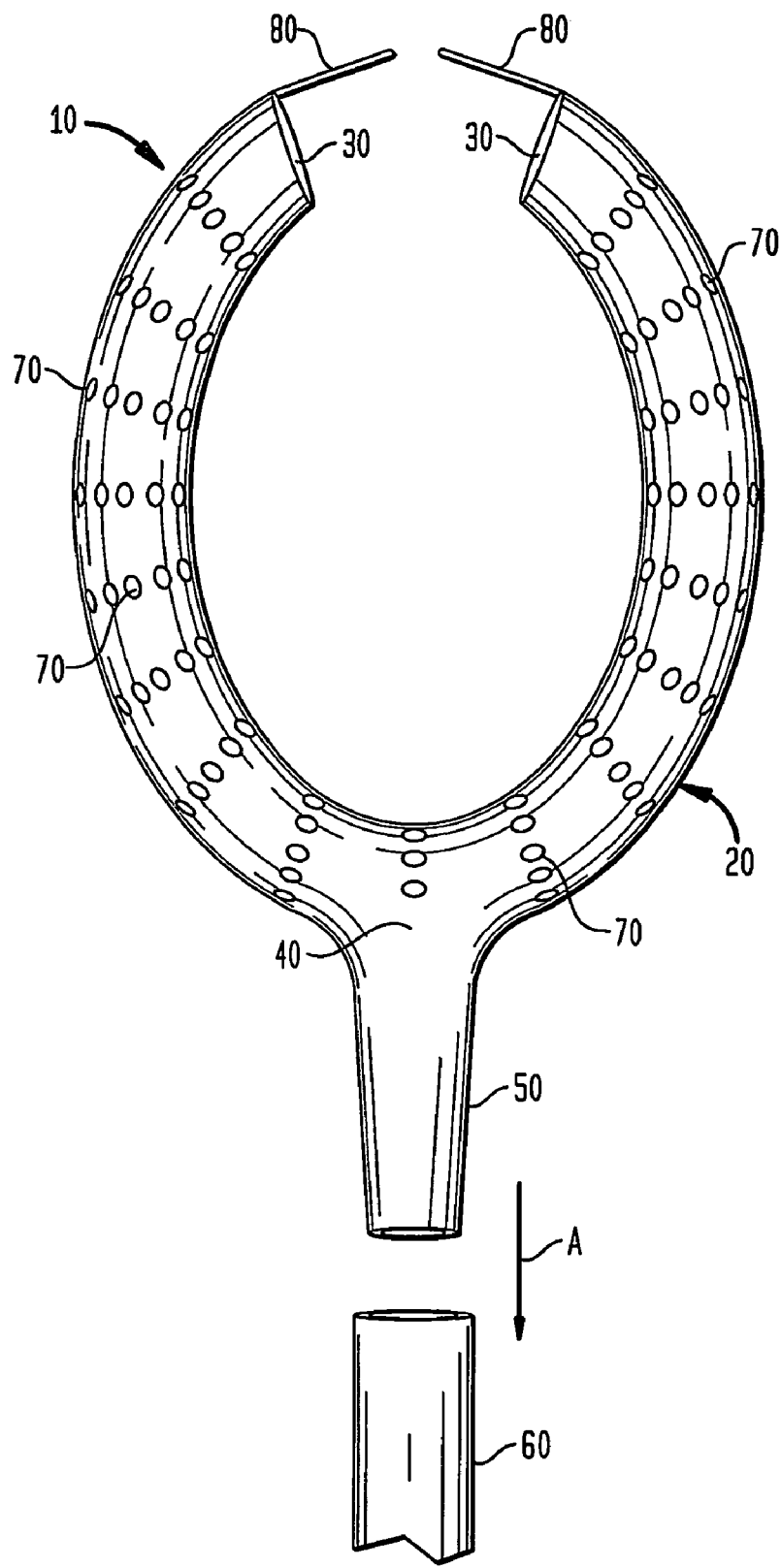
FIG. 2 is a detailed top view of the nitrous oxide scavenger apparatus shown in FIG. 1.

An embodiment of the scavenging system of the present invention is illustrated in FIG. 2, wherein the scavenging apparatus is generally designated by reference numeral 10. In this embodiment, the scavenging apparatus comprises a housing formed of tube 20 with closed free ends 30, and confluence 40 located between closed ends 30. The housing is essentially a U-shaped collar that can be attached about a patient's neck. Confluence 40 extends from the tube 20 to an outlet which may be in the form of an open-ended portion or nozzle 50. The tube can be removably attached to vacuum line 60 by inserting the nozzle 50 into vacuum line 60 in the direction shown by arrow A. The tube 20 has one or more apertures forming entry vents 70. Attached to the tube 20, at or near the closed ends 30, are tabs 80 which are releasably engagable to provide a means for securing the apparatus around a patient's neck.

The housing of the scavenging apparatus 10 can be formed with materials known in the art. For example, flexible corrugated tubing can be used to allow for some expansion and contraction of the device. Such tubing has been used in the past to connect a vacuum to a mask-type delivery and evacuation devices. The length of tubing used for the scavenging apparatus 10 should be sufficient to allow same to be positioned around a person's neck. The ends 30 of tube 20 can be sealed in any known manner. The vents 70 can be formed by perforating the tube 20. The vents 70 can be formed in tube 20 by punching holes in the tubing, or in any other desirable way, such as during manufacturing of the tube 20. The sizing and spacing of the vents 70 can be varied as desired. The vents 70 can be positioned randomly or orderly arranged on the tubing 20. Any number of vents, including a single vent of large diameter, can be provided.

The releasably engagable tabs 80 are interconnected with the tube and can be formed of any suitable material. For example, a hook and loop fastening system can be employed, wherein a hook material is applied to one tab and loop material applied to the other. However, the tube may be removably secured or retained around the patient's neck by any suitable means, for example, strings or straps which are tied together or an elastic strap which may be stretched to position the tube 20 over the patient's head.

Figure 3:
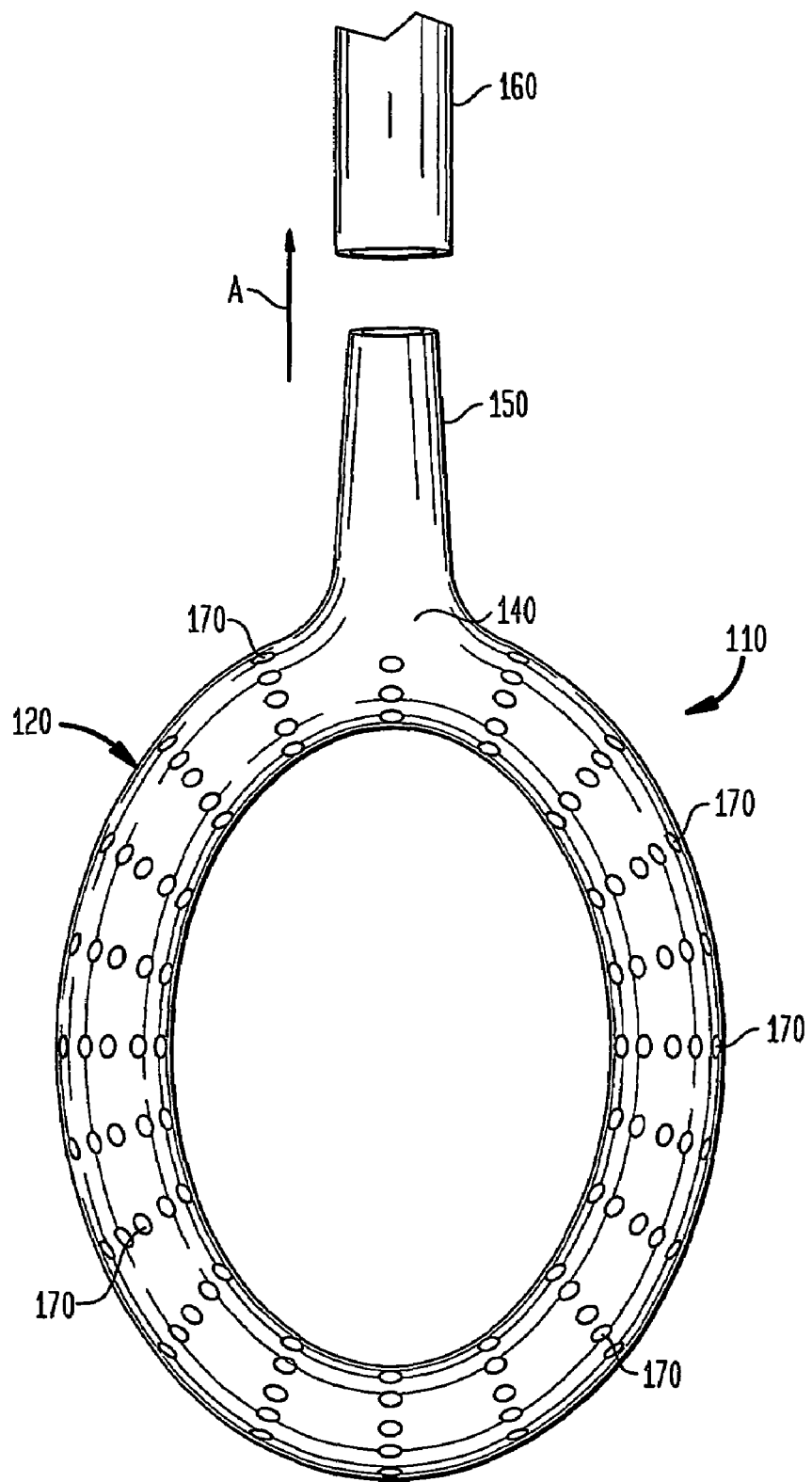
FIG. 3 shows another embodiment the nitrous oxide scavenger apparatus according to the present invention.

Another embodiment of the scavenging system of the present invention is illustrated in FIG. 3, wherein the housing of the scavenging apparatus 110 comprises a continuous tube 120. In this embodiment, the housing is essentially an O-shaped collar that can be positioned about a patient's neck. Confluence 140, which extends from the surface of the tube 120, forms a nozzle 150 for attachment to vacuum line 160 by relative movement along arrow A. The tube 120 is perforated with vents 170. The size and shape of the scavenging apparatus 110, as well as the materials and construction thereof, are similar to the apparatus shown and described in FIG. 2. The tube 120 can be placed over a patient's head to rest on the patient's body about the neck. The nozzle 150 is shown with an upward orientation, but it can be oriented in any direction as desired.

Figure 4:
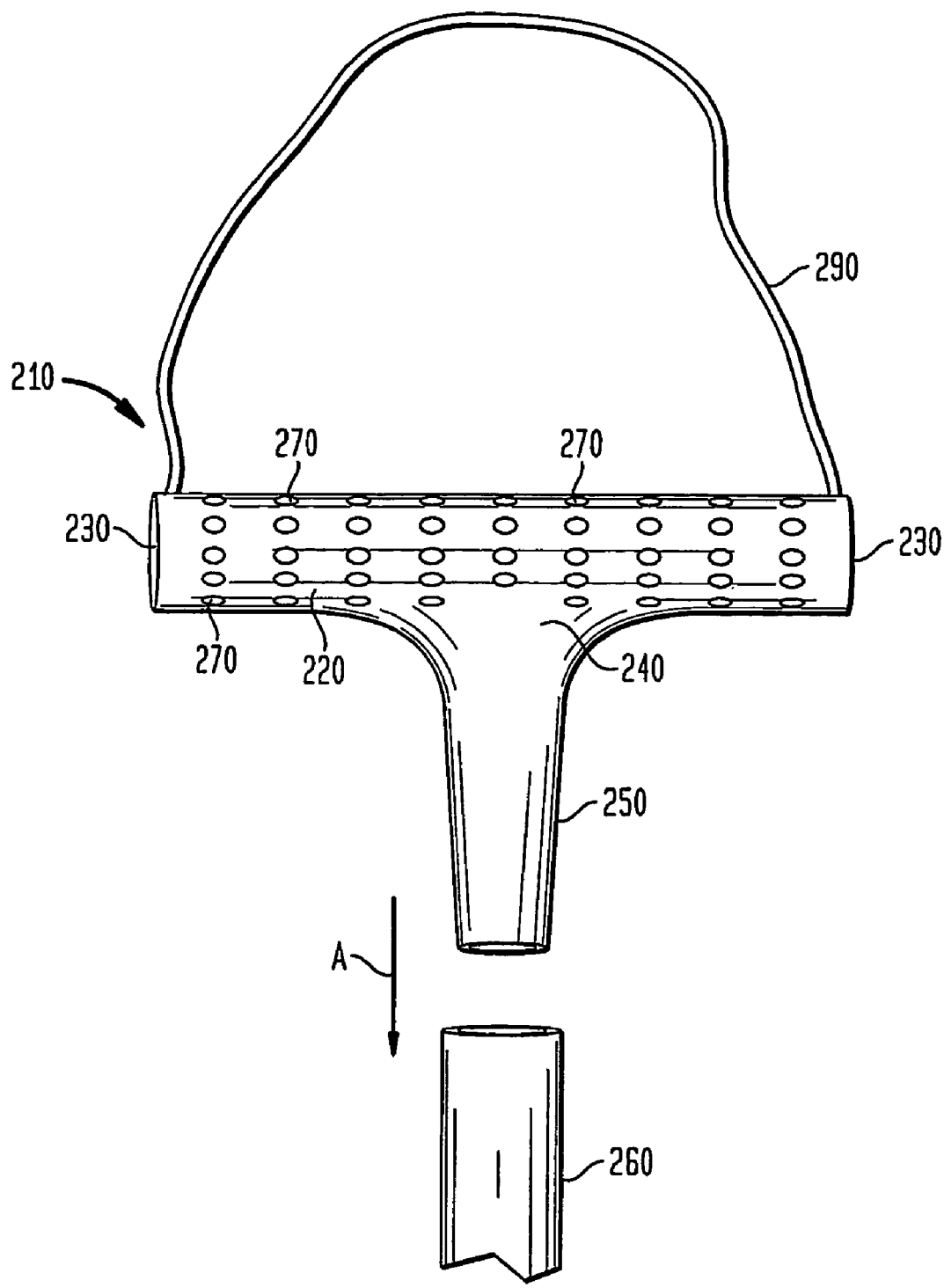
FIG. 4 shows another embodiment of the nitrous oxide scavenger apparatus according to the present invention.

Another embodiment of the scavenging system of the present invention is illustrated in FIG. 4. The scavenging apparatus, generally indicated at 210, comprises a housing formed of tube 220 having closed ends 230. Confluence 240 extends from the tube 220 forming a nozzle 250 for attachment to vacuum line 260 by relative movement in the direction of arrow A. The tube 220 is perforated with vents 270. Attached to the tube 220 near the closed ends 230 is strap 290 which may be formed of an elastic material and which provides a means for securing the apparatus around the patient's neck. The size and shape of the housing, and the materials used to make the housing, can be varied as desired.

In use, the scavenging apparatus 10, 110, 210 of the present invention is positioned about the neck of a patient and is placed into fluid communication with a vacuum source by connection to a vacuum line 60, 160, 260. Exhaled, stray and/or leaked anesthetic gases which are administered nasally are drawn into the tube 20, 120, 220 through the vents 70, 170, 270 and down through the vacuum line 60, 160, 260 to remove such gases from the proximity of the patient and any dental personnel working near the patient.

The scavenging system shown in FIGS. 1-4 is designated for use with an open circuit anesthesia gas delivery system in a non-intubating setting. It can be used concurrently with the nasal administration of nitrous oxide, which is delivered through a separate system. It functions as an adjunct scavenging system to a conventional nasal gas scavenging system, removing those gases not removed by a conventional nasal mask scavenger alone.

Figure 5:
FIG. 5 shows the scavenger apparatus of the present invention used in connection with a nose mask.

FIG. 5 shows the evacuating apparatus shown in FIGS. 1 and 3 used in connection with a nasal mask 90. The nasal mask 90 has a nitrous oxide supply line 91 and a nasal vacuum line 92. The nasal vacuum line 92 and the evacuating vacuum line 60 can be interconnected by tee connector 62, one end of which can be connected by tee line 64 to a vacuum source at a wall.

Figure 6:
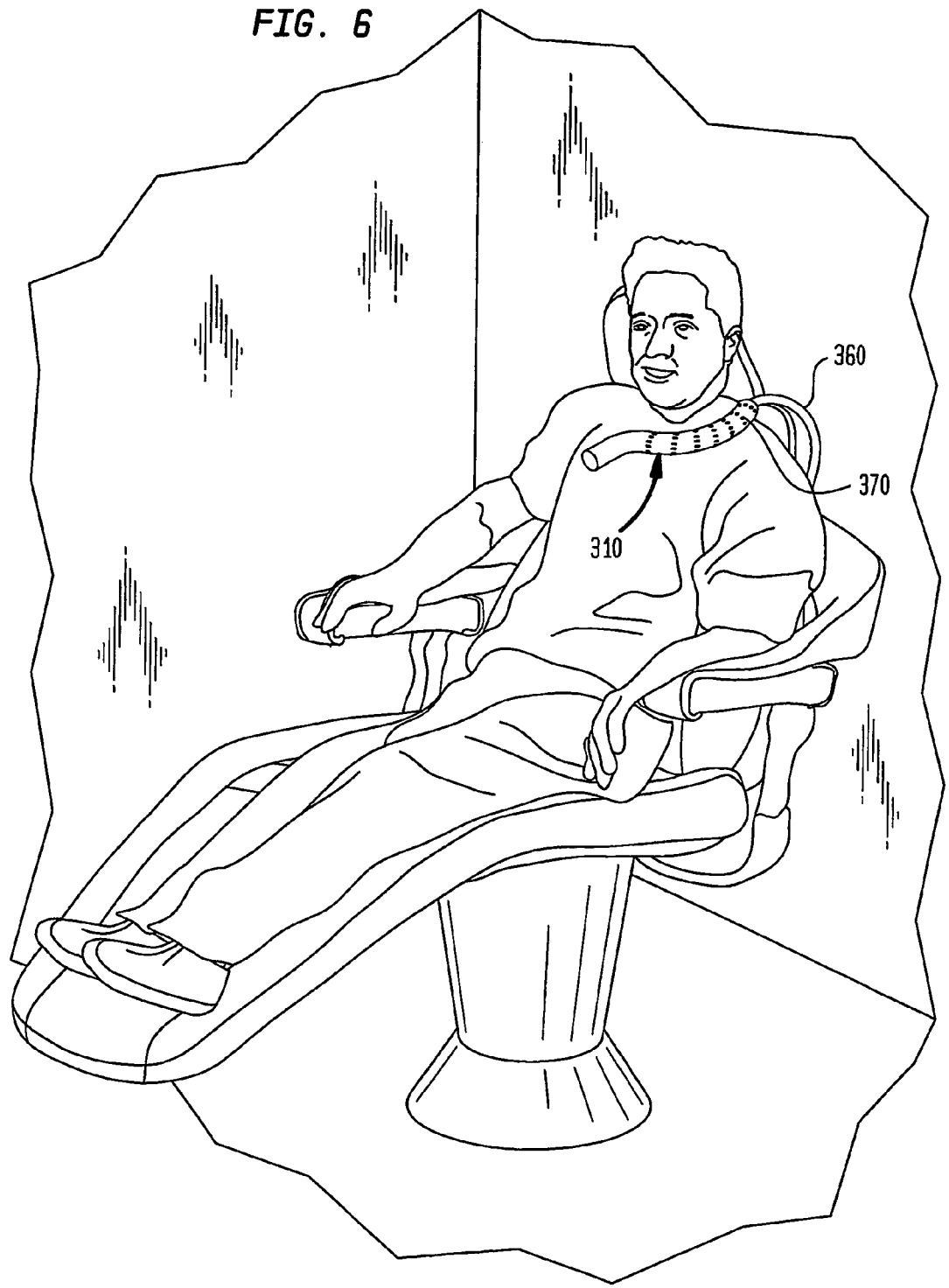
FIG. 6 shows another embodiment of the nitrous oxide scavenger apparatus according to the present invention.

FIG. 6 shows another embodiment of the evacuating apparatus of the present invention. The apparatus, generally indicated at 310, includes a housing formed of a tube connected at one end to vacuum line 360. The housing has a plurality of vents 370. The housing can be draped over a patient's chest and shoulder as shown in the figure.

The present invention also provides a method of removing anesthetic gas exhaled by a patient being nasally administered anesthetic gas and/or such gas that leaks from the system. The method comprises the steps of placing a perforated housing proximate to the mouth of a patient, connecting the perforated housing to a vacuum source, and applying a vacuum to remove exhaled anesthetic gas.

EXAMPLE

The following study demonstrates that the scavenging apparatus of the present invention reduces the levels of anesthetic gas in proximity to a subject being nasally administered the gas. In this study, 10 subjects were administered nitrous oxide according to procedures typically used in dental offices with a test mix of anesthetic gas of 40% $N_2O$/60% $O_2$. Ambient anesthetic gas in the proximity of the subjects' mouths was measured using a Medigas PM 3010 (Bacharach, Inc., Pittsburgh, Pa.) both without and with the scavenging apparatus shown in FIG. 1. Baseline levels were measured at time 0 and gas levels were measured at 3 minute intervals for 15 minutes.

Figure 7:
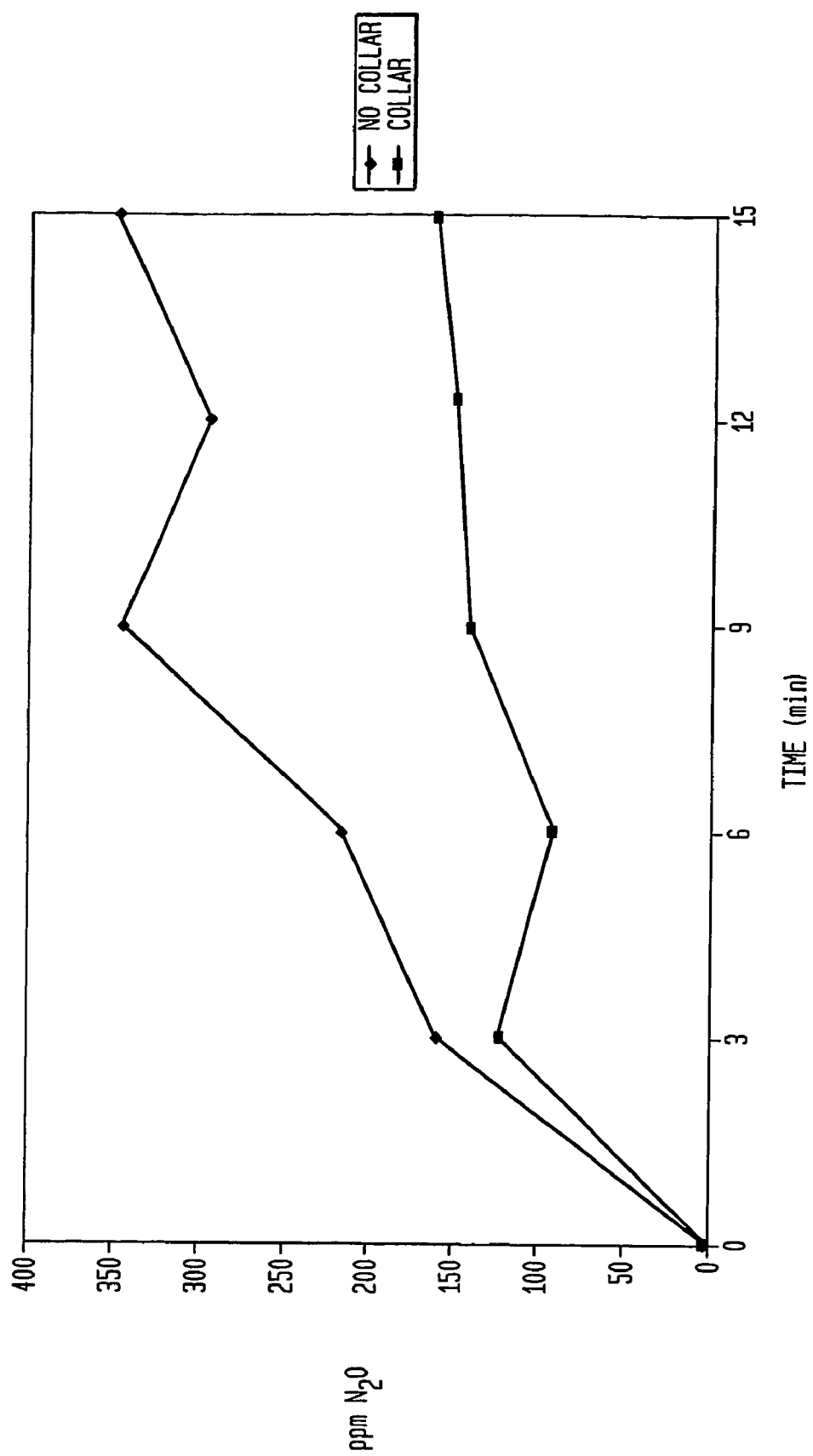
FIG. 7 shows a comparison of the average amount of $N_2O$ in ppm measured as described in the Example in subjects (n=10) without (♦) and with (■) the scavenger collar of the present invention.

The results shown in FIG. 7 demonstrate that over a fifteen minute time period, excess ambient anesthetic gas in proximity to the subject was reduced by up to 58% using the scavenging apparatus of the present invention.

Having thus described the invention in detail, it is to be understood that the foregoing description is not intended to limit the spirit and scope thereof. What is desired to be protected by Letters Patent is set forth in the appended claims.

What is claimed is:

1. A housing for use in an anesthesia scavenging apparatus, said apparatus comprising a vacuum source for withdrawing anesthetic gas exhaled by a patient from the ambient atmosphere, said housing comprising a tube having a length dimension, said tube being detachably attachable to said vacuum source, said tube having an outlet for attachment to said vacuum source, and a plurality of inlet openings or vents disposed along the outer surface of said length dimension, for the reception and ingress of said anesthetic gas to be withdrawn from said ambient atmosphere wherein said length dimension is extended and defines an arcuate shape, said tube comprises two closed ends, with said outlet positioned centrally between said closed ends, and said housing further comprises fasteners located at said closed ends of the tube for attaching the closed ends together to secure said tube about a patient's neck.

2. The housing of claim 1, further comprising a strap interconnectable with said fasteners for supporting the tube about a patient's neck.

3. A housing for use in an anesthesia scavenging apparatus, said apparatus comprising a vacuum source for withdrawing anesthetic gas exhaled by a patient from the ambient atmosphere, said housing comprising a tube having a length dimension, said tube being detachably attachable to said vacuum source, said tube having an outlet for attachment to said vacuum source, and a plurality of inlet openings or vents disposed along the outer surface of said length dimension, for the reception and ingress of said anesthetic gas to be withdrawn from said ambient atmosphere wherein the length dimension of said tube is linear in appearance and comprises two closed ends, with said outlet positioned centrally between said closed ends, so that a T-shaped appearance is defined, the housing further comprising a strap interconnectable with said closed ends for supporting the tube about a patient's neck.

4. The housing of claim 3 wherein the tube is rigid.

5. An anesthesia scavenging system, said system including a vacuum source for withdrawing anesthetic gas exhaled by a patient from the ambient atmosphere, said system comprising a tube having a length dimension, said tube having an outlet detachably attachable to said vacuum source, and a plurality of inlet openings or vents disposed along the outer surface of said length dimension for the reception and ingress of said anesthetic gas to be withdrawn from said ambient atmosphere, the tube being sized to be positioned about a patient's neck wherein the tube has two closed free ends and is secured about a patient's neck by releasably interconnectable tabs located on said closed ends.

6. The system of claim 5 wherein the tube has closed ends and is retained about a patient's neck by a strap.

7. The system of claim 5 wherein a vacuum line connecting the tube with the vacuum source is interconnected with a nasal mask vacuum line.

8. An anesthesia scavenging system, said system including a vacuum source for withdrawing anesthetic gas exhaled by a patient from the ambient atmosphere, said system comprising a tube having a length dimension and two closed free ends with fasteners for securing the tube about a patient's neck, said tube having an outlet detachably attachable to said vacuum source, and a plurality of inlet openings or vents disposed along the outer surface of said length dimension for the reception and ingress of said anesthetic gas to be withdrawn from said ambient atmosphere, the tube being sized to be positioned about a patient's neck wherein a vacuum line connecting the tube with the vacuum source is interconnected with a nasal mask vacuum line, the system further comprising a tee which connects the vacuum line from the tube to the nasal mask vacuum line, and connects both vacuum lines to a vacuum source.

9. A method of removing anesthetic gas exhaled by a patient being nasally administered an anesthetic gas comprising: placing a housing comprising a tube having two closed free ends and a length dimension and a plurality of inlet openings or vents disposed along the outer surface of said length dimension, in proximity to the mouth of a patient; connecting the perforated housing to a vacuum source: and applying a vacuum to the housing to remove exhaled anesthetic gas from proximity to the mouth of the patient wherein the step of placing the housing in proximity to the mouth of a patient comprises positioning the tube about a patient's neck and interconnecting the closed ends with fasteners located on said closed ends.

* * * * *